(12) United States Patent
Wilkens et al.

(10) Patent No.: US 7,985,219 B2
(45) Date of Patent: Jul. 26, 2011

(54) IRRADIATION DEVICE AND METHOD FOR THE TREATMENT OF ACNE AND ACNE SCARS

(75) Inventors: Jan Hennrik Wilkens, Homburg (DE); Rolf Stirner, Berlin (DE)

(73) Assignee: Spectrometric Optoelectronic Systems GmbH, Berlin (DE)

( * ) Notice: Subject to any disclaimer, the term of this patent is extended or adjusted under 35 U.S.C. 154(b) by 1298 days.

(21) Appl. No.: 10/094,431

(22) Filed: Mar. 8, 2002

(65) Prior Publication Data

US 2003/0004501 A1    Jan. 2, 2003

(30) Foreign Application Priority Data

Mar. 8, 2001    (DE) .................................. 201 09 899
May 10, 2001    (DE) .................................. 101 23 926

(51) Int. Cl.
  *A61B 18/18*        (2006.01)
(52) U.S. Cl. .................................. 606/9; 606/10; 607/88
(58) Field of Classification Search ................ 606/9–13; 607/88–95
  See application file for complete search history.

(56) References Cited

U.S. PATENT DOCUMENTS

| | | | |
|---|---|---|---|
| 3,521,111 A | 7/1970 | Tsuchihashi et al. | |
| 3,540,789 A | 11/1970 | Przybilla | |
| 4,167,669 A | 9/1979 | Panico | |
| 5,184,044 A | 2/1993 | Thomas | |
| 5,964,749 A | 10/1999 | Eckhouse et al. | |
| 6,021,344 A | 2/2000 | Lui et al. | |
| 6,050,990 A * | 4/2000 | Tankovich et al. ................ 606/9 |
| 6,166,496 A * | 12/2000 | Lys ............................... 315/362 |
| 6,183,500 B1 | 2/2001 | Kohler | |

FOREIGN PATENT DOCUMENTS

| | | |
|---|---|---|
| DE | 82 32 530.8 U1 | 4/1983 |
| DE | 41 43 168 A1 | 7/1993 |
| DE | 195 24 461 A1 | 1/1997 |
| DE | 296 13 075 U1 | 1/1998 |
| DE | 93 21 497 U1 | 10/1998 |
| EP | 0 565 331 A2 | 10/1993 |
| EP | 0 592 794 A2 | 4/1994 |
| EP | 0 726 083 A2 | 8/1996 |
| EP | 0 565 331 B1 | 1/2001 |
| WO | WO 96/13851 | 5/1996 |

(Continued)

OTHER PUBLICATIONS

V. Sigdurdsson et al., Phototherapy of Acne Vulgaris with Visible Light, Dermatology 1997, 194; Bd.3, 256-260.

(Continued)

*Primary Examiner* — David Shay
(74) *Attorney, Agent, or Firm* — Frank J. Bonini, Jr.; John F. A. Earley, III; Harding, Earley, Follmer & Frailey, P.C.

(57) ABSTRACT

An irradiation device (1) and a method for the treatment of acne and acne scars, comprising at least one source of radiation (2), the source of radiation emitting at least one broadband spectrum in the wavelength range of 320-at least 540 nm and the radiation source (2) being pulseoperable and/or movable relatively to the area to be irradiated, the pulse energy being between 0.05-10 $J/cm^2$ and the peak irradiation intensity being between 0.5 $W/cm^2$ and 100 $kW/cm^2$.

20 Claims, 10 Drawing Sheets

FOREIGN PATENT DOCUMENTS

| | | |
|---|---|---|
| WO | WO 00/02491 | 1/2000 |
| WO | WO 00/28575 | 5/2000 |
| WO | WO 00/53114 | 9/2000 |
| WO | WO 00/64537 | 11/2000 |

OTHER PUBLICATIONS

McGinley et al., Facial follicular porphyrin fluorescence: correlation age and density of Propionibacterium Acnes, Br. J. Dermatol vol. Bd.3, 437-441, 1980.

ICNIRP (IRPA)—International Commission on Nonlonizing Radiation Protection Association, Guidelines on Limits of Radiation of Wavelengths Between 180 nm and 400 nm, Health Physics 49, pp. 331-340, 1985.

Proposed change to the IRPA 1985 Guidelines on Limits of Exposure to Ultraviolet Radiation, Health Physics 56, pp. 971-972, 1989.

* cited by examiner

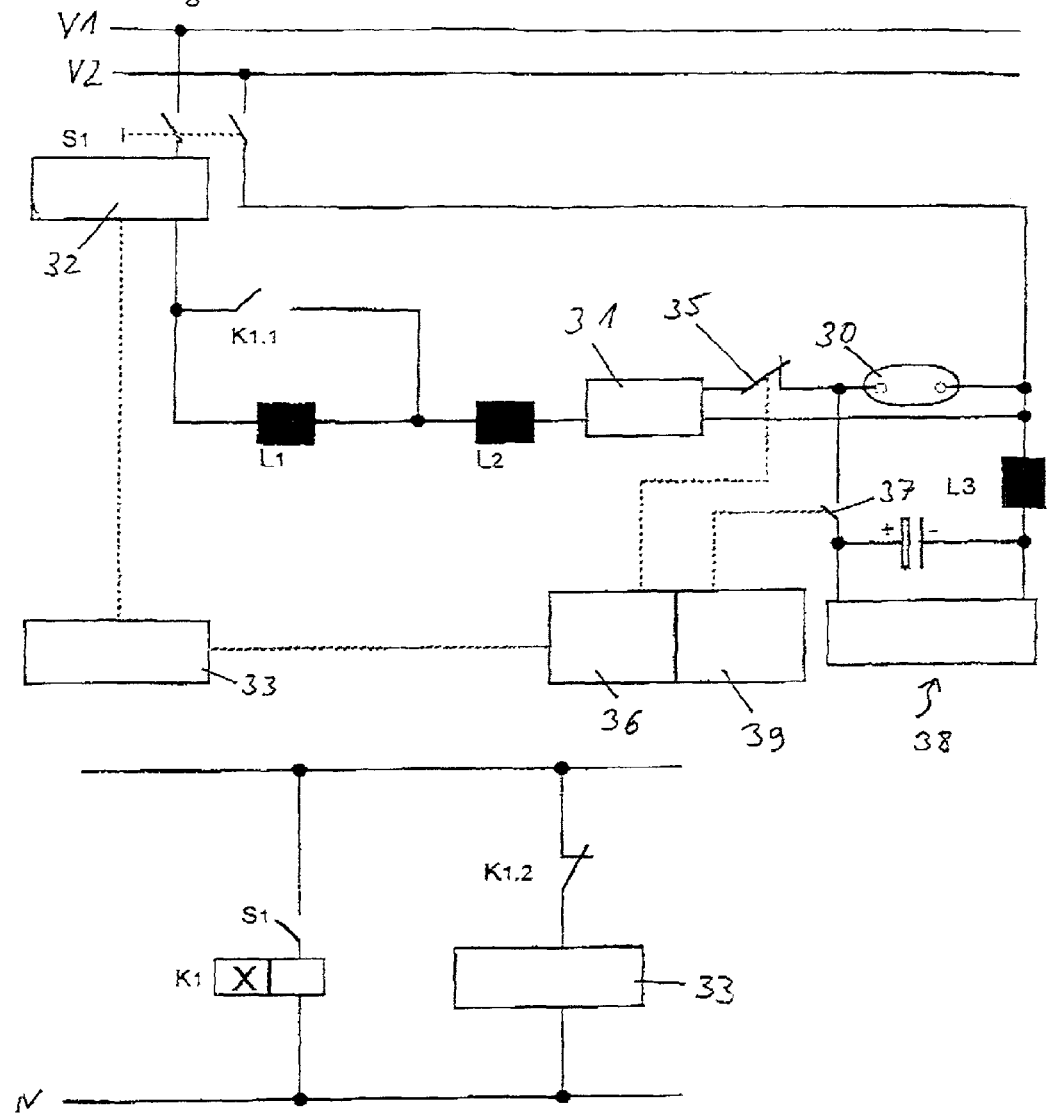

IRRADIATION DEVICE AND METHOD FOR THE TREATMENT OF ACNE AND ACNE SCARS

BACKGROUND OF THE INVENTION

1. Field of the Invention

The invention relates to an irradiation device and a method for the treatment of acne.

2. Brief Description of the Related Art

It is known to treat acne, which is a skin disease caused by proliferation of bacteria in blocked follicles of areas of the skin that are rich in sebaceous glands together with keratosis, with blue light in the range of 400-440 nm without significant proportions of UVA, with limited success.

Here we refer to the article of V. Sigurdsson et al., "Phototherapy of Acne Vulgaris with visible Light, Dermatologie 1997, 194; Iss. 3, 256-260" which includes further literature references. This form of therapy started by using red fluorescence of acne follicle as part of the dermatological examination using a woodlamp. The source determined for the fluorescence was the storage of large quantities of porphyrins in the propionbacterium acne. McGinley et al., Facial follicular porphyrin fluorescence. Correlation with age and density of *propionibacterium acnes*, Br. J. Dermatol. 1980, Vol. 102, Iss. 3, 437-441). Since the principal absorption (Soret-band) of porphyrins is around 420 nm, it was obvious for Meffert et al. to treat acne follicles with blue light. The longestwave absorption band of porphyrins is 630 nm, with a penetration depth of 4 mm, which is most favorable for photodynamic follicle treatment and is used for this purpose.

From WO 00/02491 such an irradiation device is known which comprises at least one narrowband spectrum in the range of 405-440 nm. As alternative or cumulative areas of the spectrum the wavelength intervals between 610-670 and 520-550 nm are given. For further improvement of treatment efficacy it is proposed to increase the oxygen concentration within the irradiated area by applying oxygen-enriched emulsions before or during the irradiation. The irradiation intensity for this is between 10-500 mW/cm$^2$.

WO 00/64537 describes another irradiation device for the treatment of acne. Here the afflicted area is treated with UV light in the range of 320-350 nm. The energy input given here is 1-5 J/cm$^2$. When using a laser, the pulse energy is supposed to be between 5-25 mJ/cm$^2$, so that pulse lengths of 10 ns will result in an intensity of about 2 MW/cm$^2$. The known irradiation device is based on the realization that sunlike spectra are not suitable for acne treatment, but may rather trigger an outbreak of acne.

From EP 0 565 331 B1 a device for the treatment of vascular diseases in an area of the skin is known, including a housing with an incoherent light source mounted in that housing and suitable for the emission of pulsed light for treatment, and an opening in the housing, defining a ray of light which is emitted onto the afflicted area of skin without passing through a cable of optical fibers, thus showing a wider irradiation area than devices with optical fibers, the device also including a low cutoff filter, thus cutting off the visible and UV parts of the spectrum while the incoherent light source emits a ray of light combining wavelengths between 300 and 1000 nm. The light source has an electrical connection to a pulse-formingnetwork in order to deliver a time pulse between 1 and 10 ms, the emitted ray of light producing an energy density between 30 and 100 J/cm$^2$, so that the emitted light may pass through a low cutoff filter and penetrate the skin as deeply as desired without burning of the skin, in order to heat a blood vessel under the skin in the skin treatment area and to cause blood coagulation in the blood vessel.

The blood coagulation described there is to be avoided in the treatment of acne, so that the described device is not suitable for the treatment of acne or other superficial skin diseases.

From DE 93 21 497 U1 a therapeutic treatment device is known, which is operated with an incoherent light source emitting light pulses, a preferred embodiment using flash lamps which emit light in the range of 300-1000 nm. The aim of this method is also the coagulation of blood vessels. The energy density per pulse is between 30-100 J/cm2, so that we can refer to our comment concerning EP 0 565 331 B1.

Immunologic examinations of acne patients have shown no abnormal reactions, which leads to the assumption that immunologic processes are not a factor in the development of primary acne. A secondary factor is f. e. the rupture of the epithelia of the closed comedome that will allow the contents (ceratine cells, hairs, sebum, free fatty acids and bacteria) to come into contact with the connective tissue. This causes a foreign body reaction often accompanied by an acute inflammation of the skin, which is referred to as secondary inflammatory efflorescence.

After the subsiding of the inflammation, there is a third category of acne efflorescence showing a previous serious outbreak of acne, which is cosmetically disfiguring. These scars have different appearances, such as small and comedome-like, sunken-in like wormholes or keloid-like atrophic scars covering large areas.

The known irradiation arrangements for the treatment of acne are technically elaborate and therefore costly, especially if a high energy density in specified areas of the spectrum has to be produced.

Post-inflammatory acne efflorescences cannot be treated with known irradiation devices without tissue coagulation or ablation. Therefore the problem of acne scar therapy has not been satisfactorily solved so far. The excision of crateriform acne scars is invasive and goes with a high risk of infection. Facial acne scars can be treated with high-speed dermabrasion devices; keloid acne scars are often treated cryosurgically with liquid nitrogen. Both techniques are also elaborate as well as costly.

SUMMARY OF THE INVENTION

The invention is based on the technical problem of providing an irradiation device and a method for the treatment of acne and acne scars that are cost-efficient and show a high treatment efficacy.

Here, the radiation source is designed as a broadband radiation source with wavelengths in the range of at least 320-at least 540 nm which is pulse-operable and/or with the possibility of relative motion to the area to be treated. The pulse energy per pulse is between 0.05 10 J/cm$^2$ and peak radiation power of the optical pulses lies between 0.5 W/cm$^2$ and 100 kW/cm$^2$. At least 320 nm means, that the radiation source can emit shorter wavelengths, but these wavelengths are not transmitted to the area to be treated but cut off beforehand. Wavelengths longer than 540 nm, on the other hand, can be emitted. The invention utilizes the fact that in contradiction to scientific reports pulse operation resp. pulsed irradiation using the same energy as input cw-radiation will induce an increase in the generation of singlet oxygen of several orders of magnitude.

It now appears that, surprisingly, that by using pulse operation the average radiation power can be pushed below the threshold known from scientific reports whereas at the same time the efficiency is increased. Contrary to WO 00/64537, the visible parts of the spectrum are also treatment efficient, and therefore the invention can draw on inexpensive broadband radiation sources, making costly lasers or filters expendable. The cause for outbreaks of acne under solar-like radiation sources is assumed to be not in the visible part but in the UVB-part at 320 nm, which the invention does not use. Another advantage over WO 00/02491 is a higher performance, i.e. more energy from the blue part of the spectrum reaching the follicle. Since the hair follicles are situated in the deeper layers of the skin, only a fraction of the blue part of the spectrum between 400-500 nm reaches the follicles due to very high dermal absorption. Therefore, irradiation devices with a pure blue spectral emission have to use high power and even then the results often remain modest. This is only partially due to the low penetration depth of the blue part of the spectrum, but may be more likely related to the presence of a threshold dose due to antioxidant dermal mechanisms. This possibly explains the poor results of Sigurdsson who employed only low radiation power below or within the range of this threshold.

Unexpectedly, this invention teaches that mean irradiation levels which are one order of magnitude lower than the threshold of 60 mW/cm$^2$ described in WO/022491 and below the irradiation levels employed by Sigurdsson and Meffert can be very effective if the peak pulse power exceeds the described threshold levels for a short time only. Clinical results show that the efficacy of a pulsed-light acne therapy compared to a cw-treatment with an identical spectrum can be increased by a factor of 10-20. The efficacy of acne therapy described in WO 00/02491 possibly relates to the killing of superficial bacteria through the blue part of the spectrum, whereas follicles can only be reached by the aforementioned green and red parts of the spectrum between 520-550 nm resp. 610-670. Pulsed irradiation is much less affected by constant threshold off-set than cw-irradiation, since the fractional contribution of the off-set is much smaller with pulsed irradiation than with cw-radiation. Therefore, the pulsed blue light which reaches the follicle can generate singlet oxygen more efficiently.

According to the invention, it is possible to treat not only inflammatory acne, but also the post-inflammatory cosmetically disfiguring acne scars with good results. Unexpectedly there was a discoloring of the pigmented scars which flattened simultaneously. Most likely, the pigments are bleached by singlet oxygen generated by the blue irradiation. In addition, there appears to be a reactive-oxygen species-mediated histological remodeling of the skin. Signs of skin-aging, wrinkles, epidermal and dermal atrophy, coarseness and flabbiness of the skin and increased pore diameter are decreased or reduced. The unexpected skin rejuvenation appears to be related to a dermal metabolic change which involves extracellular matrix proteins. There is an increase in procollagen, collagen and collagenase, which reflects the irradiation-induced remodeling of the skin. The result is a partial or complete reduction of the disfiguring skin changes.

The technical specification of power and energy density always relates to the irradiated skin surface. The irradiation device will preferably be put into direct contact with the skin. Preferably, the effective pulse lengths are between 1 μs-500 ms. This relatively broad range stems from the different preferred effective pulse lengths for pulsed radiation sources and for relative motion in the form of a scanning device. The scanner, however, is preferably used for the treatment of skin diseases covering larger areas.

The preferred effective pulse lengths for flashlamps are between 1 μs and 50 ms, more preferably between 10 μs and 10 ms and most preferred between 100-600 μs, with the pulse on/off periods being asymmetric.

In the scanner embodiment the preferred effective pulse lengths are between 1 ms and 500 ms, more preferably between 20-100 ms. Effective pulse length means the period of time between the achievement of 50% of maximum performance and the drop to 50% of maximum performance. The off-period between pulses are longer than the effective pulse length in order to allow the diffusion of depleted oxygen. The ratio of pulse on/off periods is preferably between 3-3000 for the scanner and 100-100,000 for the flashlamp. Another effect is the thermal cooling of the irradiated area during the pulse-off period, so that necrosis does not occur.

In another preferred embodiment the pulse frequency for the radiation source is between 0.01-100 Hz, more preferably between 0.05-50 Hz and further preferably between 0.3-3 Hz, using shorter effective pulse lengths and lower pulse energies with higher frequencies.

Just as the effective pulse lengths are dependent on the use of either a pulsed radiation source or a source with relative motion, the preferred irradiation intensities resp. peak power densities per pulse are also different.

In embodiments with a pulsed radiation source the irradiation intensity per pulse is between 1 W/cm$^2$-100 kW/cm$^2$, preferably between 50 W/cm$^2$-50 kW/cm$^2$, more preferably between 500 W/cm$^2$-10 kW/cm$^2$ and most preferably between 1 kW/cm$^2$-5 kW/cm$^2$. The energy density per pulse is between 50 mJ/cm$^2$-10 J/cm$^2$, preferably between 100 mJ/cm$^2$-1 J/cm$^2$ and most preferably between 300-1000 mJ/cm$^2$.

In embodiments which employ a scanner which in addition may allow for the pulsing of the radiation source while moving, the power densities per pulse are preferably between 500 mW/cm$^2$-5000 W/cm$^2$ and between 1-500 W/cm$^2$ and more preferred between 2-300 W/cm$^2$ and even more preferred between 3-100 W/cm$^2$. The energy density per pulse is between 50 mJ/cm$^2$ and 10 J/cm$^2$, preferably between 100-3000 mJ/cm$^2$ and more preferred between 150-100 mJ/cm$^2$ and most preferred between 200-500 mJ/cm$^2$.

The generation of longer effective pulse lengths is almost impossible using the known flashlamps. The generation of these pulse lengths may be useful to selectively warm the sebum containing follicle and the hair shaft in order to soften the obstructing sebaceous concrements and induce a reduction of sebum production. Another positive effect may be a decrease in keratinization of epithelial cells in the hair shaft area. These longer pulse lengths may be simulated according to the desired thermokinetic effects through a precise control of the pulse forming network. For example 100 pulses with an effective pulse lengths of 100 μs and a pulse-off time of 900 has will be generated with no pulses following for the next 10-1000 ms is will be between 50-300 μs.

In another preferred embodiment the radiation source is a xenon flashlamp. These known xenon flashlamps are inexpensive and emit enough light in the preferred spectral range between 320-450 nm resp. 320-670 nm. Such flashlamps are mentioned in U.S. Pat. No. 4,167,669 and EP 0 565 331, but the described pulse energies are too high for the teaching of this invention. Xenon flashlamps with a medium to high power load can be spectrally compared to the radiation of a black body. Therefore, xenon flashlamps typically emit between 200-2000 nm. Due the cell toxicity of the wavelength between 200-320 nm, this wavelength band has to be filtered. Furthermore it is possible to dope the xenon flashlamps with metals or metal halides in order to specifically amplify certain spectral regions. Very suitable therefore are gallium, indium and/or their halides.

In another preferred embodiment the radiation source is equipped with a device for the suppression of the spectral regions between 320-400 nm and/or transformation of this UV-emission into visible radiation. This takes account of the fact that all possible cellular adverse effects of UV radiation can be avoided completely without a reduction of the device efficacy. Known inexpensive UVA filters may be used to filter the UVA spectral parts. Preferably, the said UVA parts of the spectrum are transformed into the visible spectrum by use of suitable inorganic phosphors or organic laser dyes. Well-tried are foils made of silicone elastomers which have been doped with anorganic phosphors. Due to the principal absorption of the porphyrins around 420 nm, preferably blueemitting phosphors are used and may be combined with green and red phosphors which emit between 520-550 nm and/or 610-670 nm. In an alternative embodiment fluorinated polymers such as PTFE may be used instead of silicone elastomers. When using inorganic phosphors, for the transformation of the undesired spectral bands, other radiation sources such as deuterium flashlamps may be used. These flashlamps have a high efficiency in the UV spectral regions which can be transformed into preferred spectral regions by the aforementioned phosphors.

Another possible irradiation source is an overload-pulsed mercury iodide-gallium lamp. Overload is defined here as the maximum discharge energy being 3-1000 times the nominal lamp current, the pulse discharge energy being preferably between 15-1500 A/cm$^2$ cross-sectional area of the discharge vessel. A description of same standard metal-vapor mercury halide lamps can be found f. e. in U.S. Pat. No. 3,521,111; U.S. Pat. No. 3,540,789 and WO 96/13851.

U.S. Pat. No. 5,184,044 shows that with regard to the lamp geometry, the lamp performance of 20 W and the voltage drop of 55 V a lamp current of 8/A cm$^2$ cross-sectional area of the discharge vessel corresponds to a maximally recommendable lamp load, since there is already an inversion of the indium spectrum. A further increase of current density would amplify the inversion up to total deletion.

Those lamps have not been overload-operated so far, since it was known from plasmaphysical studies that narrowband emission spectra can only be produced when using relatively low excitation energy. Overload operation causes such an increase of vapor pressure in the discharge plasma that the line emission is absorbed by the surrounding plasma and there is a paradox considerable reduction or even complete deletion of the resonance line emission under high discharge pressures. Examples include the mercury emission at 254 nm, the sodium emission at 488 nm and the indium emission at 450. Here, even moderate overload leads to loss of spectral intensity in the aforementioned emission lines.

Unexpectedly, it was discovered that gallium iodide-doped mercury medium-resp. high pressure lamps do show neither broadening nor an inversion of the gallium emission at 403 and 417, even if the overload is 100-1000 times above normal operating conditions. A galliumiodide-doped mercury discharge lamp run under normal conditions with a discharge current of 1.5 A/cm$^2$ cross-sectional area of the discharge vessel could be run in pulse operation mode with 1000 A/cm2 cross-sectional area of the discharge vessel without reduction or inversion of the gallium emission lines. A possible explanation relates to the fact that metallic gallium has a boiling point of 2200° C. so that the gallium vapor pressure can be neglected even under pulse operation of the lamp. However, there is a disintegration of mercury iodide into mercury and iodine. During the plasma discharge, iodine forms an instable compound with gallium, galliumtriiodide. GaI3 shows a marked increase of vapor pressure even at rather low temperatures. The absent inversion of the gallium emission could be explained by the fact that GaI3 is only stable up to a certain pressure and there is a rapid disintegration into gallium and iodine if the pressure is increased any further. Therefore a relatively stable gallium vapor pressure can be maintained even if there is rapid temperature increase during pulse operation. After the disintegration of the compound, GaI3 there is a condensation of metallic gallium which does not take part in the discharge and possible self-absorption of the gallium emission. This unexpectedly discovered effect could therefore be related to a paradox constant vapor pressure covering a temperature range between 200 and almost 2200° C. Mercury iodide disintegrates early into mercury and iodine, so that there is always iodine available to form a compound with the gallium. Mercury pressure therefore may increase rapidly with the energy load, thus providing excitational energy for the gallium emission. Due to the relatively stable gallium vapor pressure, most of this energy is emitted as gallium spectrum lines at 403 and 417 nm.

During overload operation, a temporary overheating occurs, particularly of the tungsten electrodes, which can emit considerably more heat at a rise of temperature, according to Planck's law. Therefore, a modulated lamp may be operated with an increased base load, since it is due to the temperature rise that the emission of input energy is considerably more efficient than in a normaloperated lamp. It so has turned out that a 1 kW-lamp can be operated with a steady load of 2-20 kW. Spectral measurements have shown the following: When a 1000 W mercury iodide gallium-doped lamp is cw-operated, approx. 400 mW/m2 in the spectral range of 400-440 nm reach the skin. This irradiation intensity can be decreased in simmer mode to an average irradiation intensity of 2-4 mW/cm$^2$, while the irradiation intensity during pulse load is temporarily increased by up to four to five orders of magnitude, so that irradiation intensities between 2 and 400 W/cm$^2$ reach the skin. The preferred ratio of pulse lengths lies between 3 and 300. This simple pulsed light source is also suitable for other technical applications such as f. e. dental curing, typographic applications, sealing of surfaces, pipe repair with light-cured tubing, plastic curing in the DVD production sector as well as the acceleration of other photochemical reactions that can be influenced by radical mechanisms of photoabsorption in the UV-blue range of the spectrum.

The ratio of gallium, resp. gallium additive and mercury should preferably be 1:10 to 1:100. In the performance range of 400 W the preferred ratio of components is 1-5 mg gallium iodide to 44 mg mercury.

Another typical lamp consists of a cylindrical quartz tube with diameter λ13.5 mm and a discharge vessel with a volume of 20 cm$^3$. The distance between the electrodes is 14 cm. This lamp is filled with 20 mg Hg, 3 mg mercury iodide, 1 mg gallium and argon with a pressure of 3.57 mm Hg.

The efficacy of the radiation device can be further increased by enhancement of the oxygen concentration. In addition to the measures described in WO 00/02491 this can be accomplished through oxygen inhalation via an oxygen mask.

Pulse irradiation leads to a perceptible increase in skin temperature, so that preferably a cooling device will be used for the irradiated area. This can be a simple air cooling. The cooling device may be assigned to the radiation source. This could be air cooling or other thermal measures such as a heat sink. Furthermore the fluorescent foil is preferably cooled by air or more preferable by water.

In order to increase the emitted power towards the treatment area, a reflector will be added to the radiation source. A preferred type of reflector is a parabolic reflector with the radiation source being mounted next to the focus of the parabolic reflector. Other reflectors such as hemispheric of similarly formed reflectors can be used.

The irradiated area for a mobile system is in the range of 1-200 cm2, since there is an increase in penetration depth if one uses area irradiation in comparison to point irradiation which is advantageous for the reaching of the deeper follicles. A mobile embodiment allows the sequential irradiation of different acne areas, which are normally located in the facial area, the neck area as well as in the area of the upper back and chest.

Alternative embodiments are possible in order to irradiate larger areas simultaneously. A possible embodiment comprises a large number of small flashlamps, f. e. 30-60 xenon flashlamps which are sewn into a tissue. The tissue may consist of PTFE or PTFE derivatives. High reflectivity can be achieved through metal vaporization which leads to the desired air transmission with simultaneous water resistance impact. If a multitude of small radiation sources are used next to the irradiated object, it is possible to omit an imaging reflector. With the aid of soft, radiation-transparent distance adaptors, f. e. made of silicone elastomers, cooling of the filters, of the luminescent foils as well as the irradiated skin areas is achieved with standard air coolers such as CPU coolers.

In another preferred embodiment a device for the generation of mechanical oscillations is associated with the radiation device. Preferably, the mechanical oscillations are time-shifted compared to the optical pulses. This mode allows the warming and liquifying of the hardened sebum. The following mechanical oscillation then leads to an extraction of the liquified sebum from the pore.

In a preferred embodiment, this device is an electrodynamic transducer. Opposite flat coils exert push or pull pressures on the skin surface by means of a suitable electrical energization. The driving of the coil can use the current of the radiation device. Alternatively, the device can be built as a photomechanical transducer where the rapid extension of a material by the optical pulse is used to generate mechanical oscillations.

BRIEF DESCRIPTION OF THE DRAWING FIGURES

The invention is explained by describing a preferred example.

FIG. 10 is a schematic illustration of an alternative circuit design with capacitor bank.

DETAILED DESCRIPTION OF THE PREFERRED EMBODIMENTS

Figure 1:
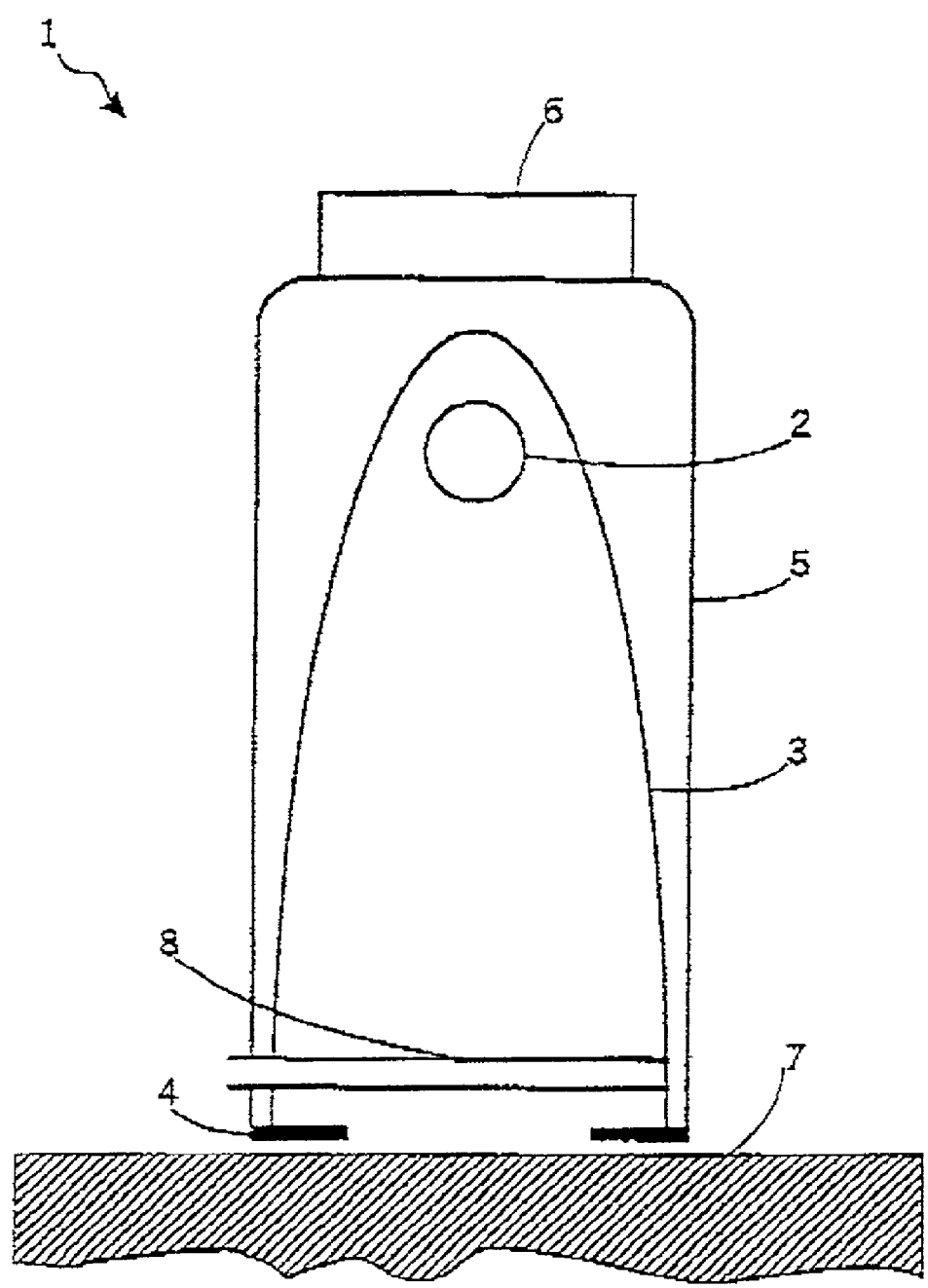
FIG. 1 is a cross-section through the irradiation device.

The irradiation device 1 comprises a broadband irradiation source 2 which is preferably a xenon flashlamp. The irradiation source 2 is mounted in the focus of a parabolic reflector 3 which is open on the side averted from the focus. The exit area at the open end of the parabolic reflector 3 is preferably defined through an adjustable shutter. The adjustable shutter can adjust the area to be irradiated. The irradiation source 2 and the paraboloid reflector 3 are mounted in a housing 5. The housing 5 comprises a handpiece 6 by means of which the irradiation device 1 can be placed on the area to be treated 7. Between the radiation source 2 and the area to be treated 7 there is a luminescent foil 8 arranged which is doped with luminescent particles. The luminescent foil 8 can also be arranged in the proximity of the radiation source 2 or the shutter 4. Preferably, the luminescent foil 8 is arranged in a way that makes it easy to replace. This simplifies the necessary replacement due to aging but also the flexible use of luminescent foils with different luminescent particles.

Furthermore, an externally mounted luminescent foil 8 can easily be disinfected. The electrical connectors and the pulse forming network for the generation of variable pulsewidths are not shown here for reasons of clarity.

Figure 2:
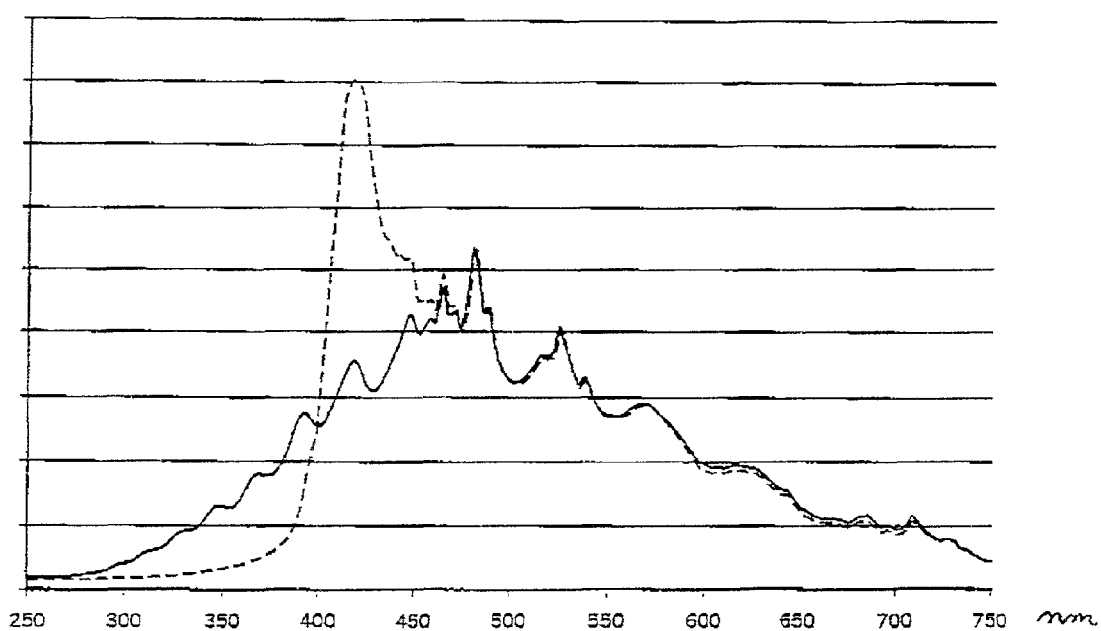
FIG. 2 shows a Spectrum of the radiation source with and without luminescent foil.

FIG. 2 shows a spectrum of a used xenon flashlamp with and without luminescent foil. the spectrum of the luminescent foil is shown as a dotted line. The luminescent foil is a silicone elastomere which is doped with anorganic phosphors which emit preferably in the blue spectral range between 400-450 nm. The luminescent foil cuts off the UV spectral range between 280-400 nm almost totally and transforms said UV range into the visible blue range between 400-450 nm. The remaining near-infrared radiation is not shown here.

The xenon flashlamp is timed with a frequency of 0.01-100 Hz preferably between 0.1-10 Hz with an effective pulse length of only 10 μs-10 ms. The optical pulse energies lie between 0.5-10 $J/cm^2$, preferably between 1-3 $J/cm^2$. The acne treatment is given over a period of several days or weeks with a daily treatment between 1-60 minutes, preferably between 5-10 minutes.

Figure 3:
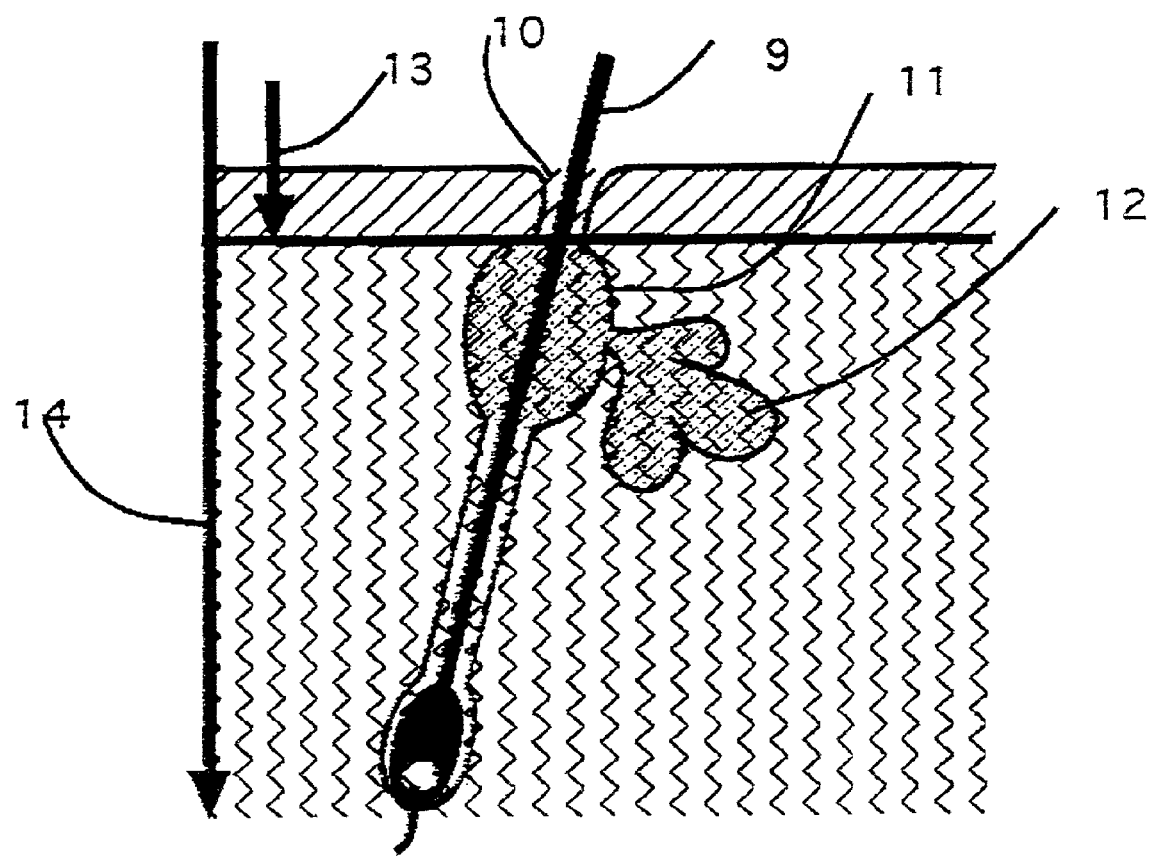
FIG. 3 is a cross-section through skin with an acne follicle.

FIG. 3 shows a cross section of the skin in the proximity of hair. The hair 9 is connected via narrowed ductus 10 with an inflamed and sebum-congested hair shaft 11 with an enlarged and inflamed sebaceous gland 12. Cw operation with blue light leads to a functional absorption of the blue light due to low penetration depth (1/e) and due to the dermal threshold for blue light. This is schematically shown by the short arrow 13. In pulse mode, however, the peak pulse energy is much higher than the average energy of the cw-operation so that the constant off-set due to dermal thresholds is much lower.

Therefore the remaining effective power after off-set substraction is increased and a larger fraction of blue light reaches the deeper areas of the hair shaft 11 resp. the sebaceous gland 12. This light can increase the local generation of singlet oxygen which is demonstrated by the longer arrow 14.

Figure 4:
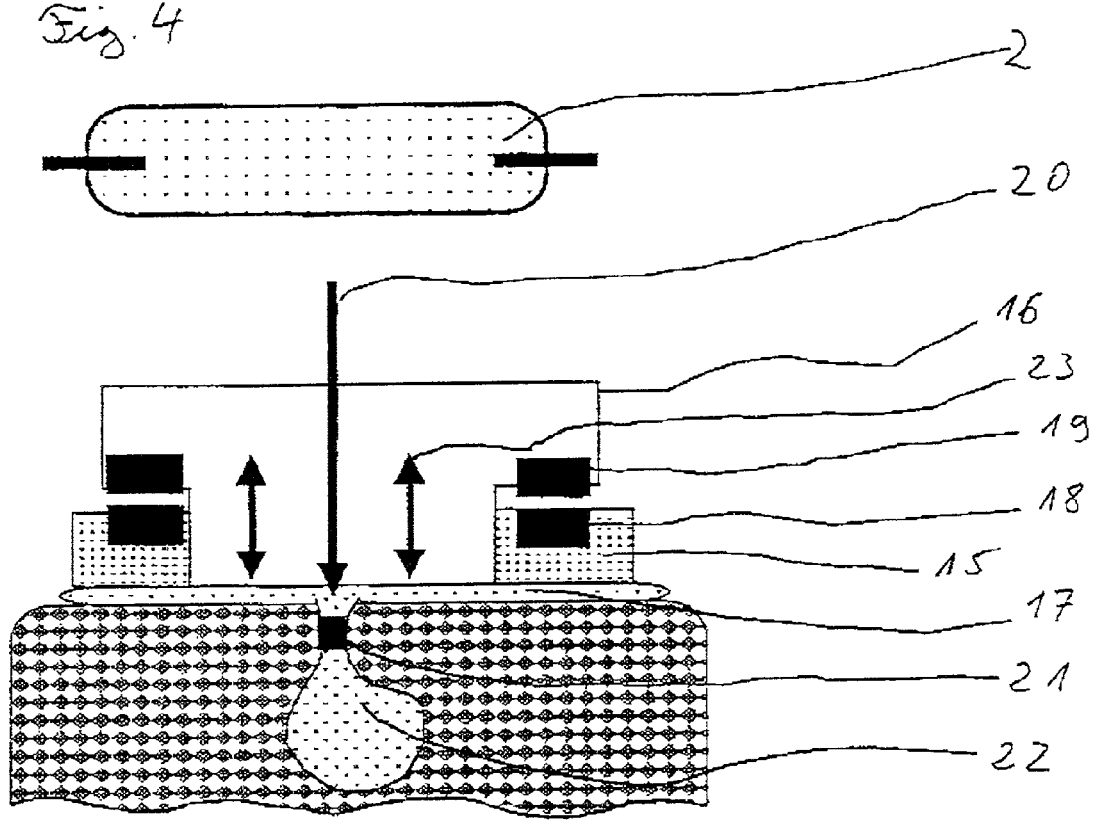
FIG. 4 is a schematic illustration of an electrodynamical transducer.

FIG. 4 shows the principal scheme of an electrodynamic transducer. The device for the generation of mechanical oscillations comprises a frame 15 and a transparent incompressible pistil 16 which is movable within the frame 15. The pistil 16 is partially coupled to the skin via an ultrasound gel 17. At the margin of 5 the frame 15 resp. pistil 16, flat coils 18 and 19 are mounted in opposite to each other. The pulsed light 20 which is emitted by the radiation source 2 is absorbed by the sebum plug 21 and the sebum 22 below. The sebum plug 21 absorbs light within the visible part of the spectrum and in the near infrared, whereas the sebum 22 preferably absorbs within the NIR. This leads to a warming and liquification of the sebum plug 21 resp. the sebum 22. Due to a suitable polarity between the flat coils 18 and 19 there is an attraction resp. repelling between the flat coils 18 and 19. Since the frame 15 is immobile the pistil 16 either moves towards or away from the skin which is shown by the double arrow 23. By these vibrations the liquified sebum plug 21 is loosened and the sebum plug 21 and the sebum 22 are removed from the pore.

Figure 5:
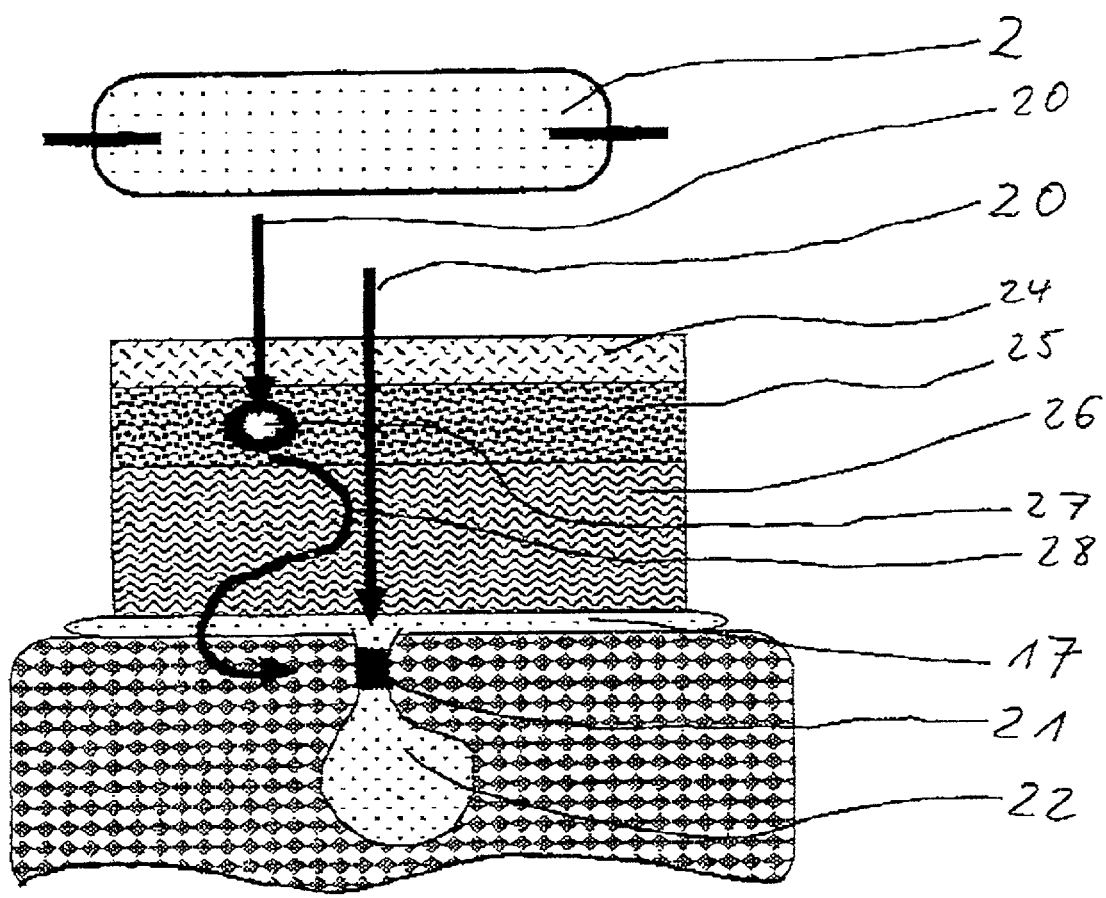
FIG. 5 is a schematic illustration of a photoelastic transducer.

FIG. 5 shows an alternative embodiment for the generation of mechanical vibrations. The device comprises a first layer 24 of an optically transparent material with high sound conductive velocity, a second layer 25 made of an optically transparent carrier material and a third layer 26. On and/or in the second layer 25 light-absorbing dye molecules 27 are arranged which can be arranged in stripes or concentric rings. Due to the absorption of the pulsed light there is a sudden thermal expansion of the dye molecules 27 which leads to the build-up of a pressure wave 28. This pressure wave 28 is non-directional, expanding upwards and downwards. The part of the pressure wave 28 which expands upwards is reflected by the first layer 24 and again downwards. The third layer 26 generates a specific phase-distortion between the light and pressure wave 28 so that the pressure wave 28 reaches the sebum plug 21 only after the plug having been warmed and liquified. The third layer 26 is expendable if near field effects are utilized specifically. This can be accomplished by the generation of local maxima which are closer to the skin surface than a $\lambda/2$ using frequencies in the kHz range.

Figure 6:
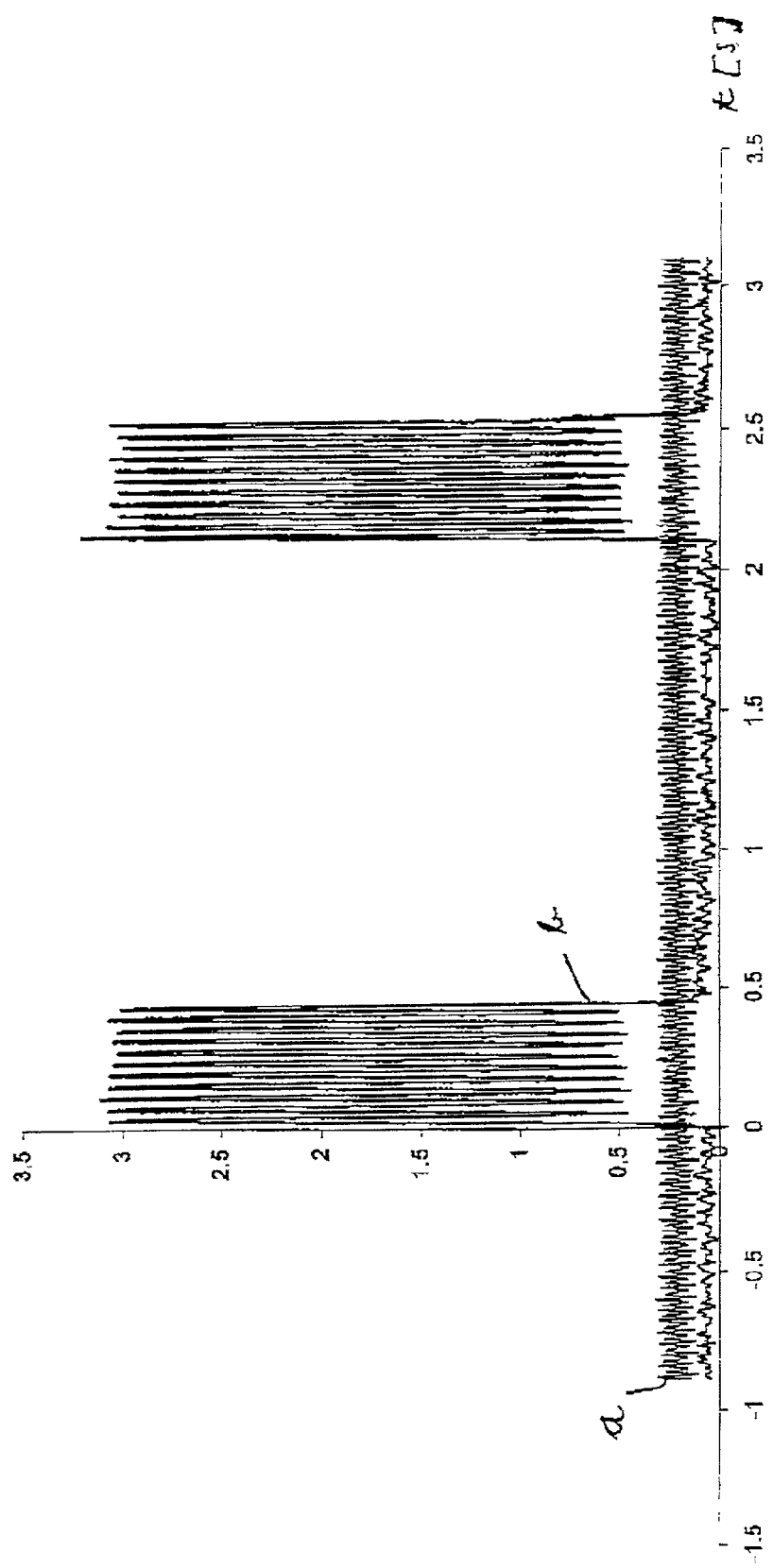
FIG. 6 is a graph illustrating the effect of cw-operation and pulsed operation on the relative radiation intensity of a gallium doped mercury discharge lamp.

FIG. 6 displays a comparison of the relative irradiation power of a 1000 W galliumiodide-doped mercury lamp in continuous mode operated at 1000 W (curve a) and in pulsed overload operation (curve b). The average power in pulse operation mode is 1500 W. It is obvious that even a small overload induces a marked rise of the optical emission.

Figure 7:
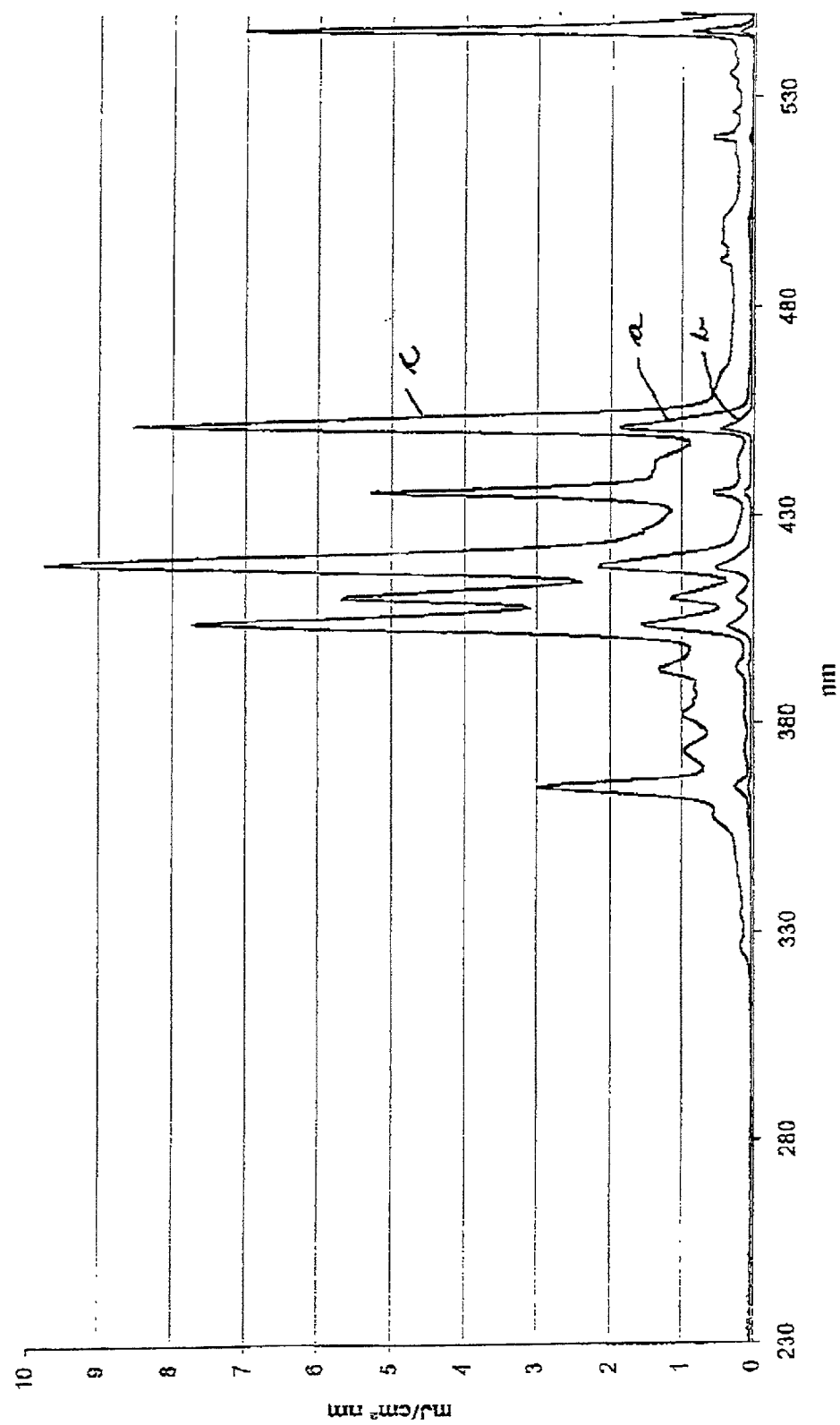
FIG. 7 is a graph illustrating the spectral energy density of a gallium iodide-doped mercury lamp at different power loads.

FIG. 7 shows the spectral energy density of a galliumiodide-doped mercury lamp with a normal operating power of 1000 W if the input power is changed. Curve a) represents the spectral energy density under cw-operating conditions at 1000 W. Curve b) shows the spectral energy density at a lowered load of 100 W, and curve c) displays the spectral energy density with an input power of 10 kW. Low load and overload operation were performed in cw-mode. It can be seen that in both cases the spectral lines of the gallium emission remain stable and there is no inversion of spectral lines. Furthermore, there is an enormous proportional increase of the emission.

Figure 8:
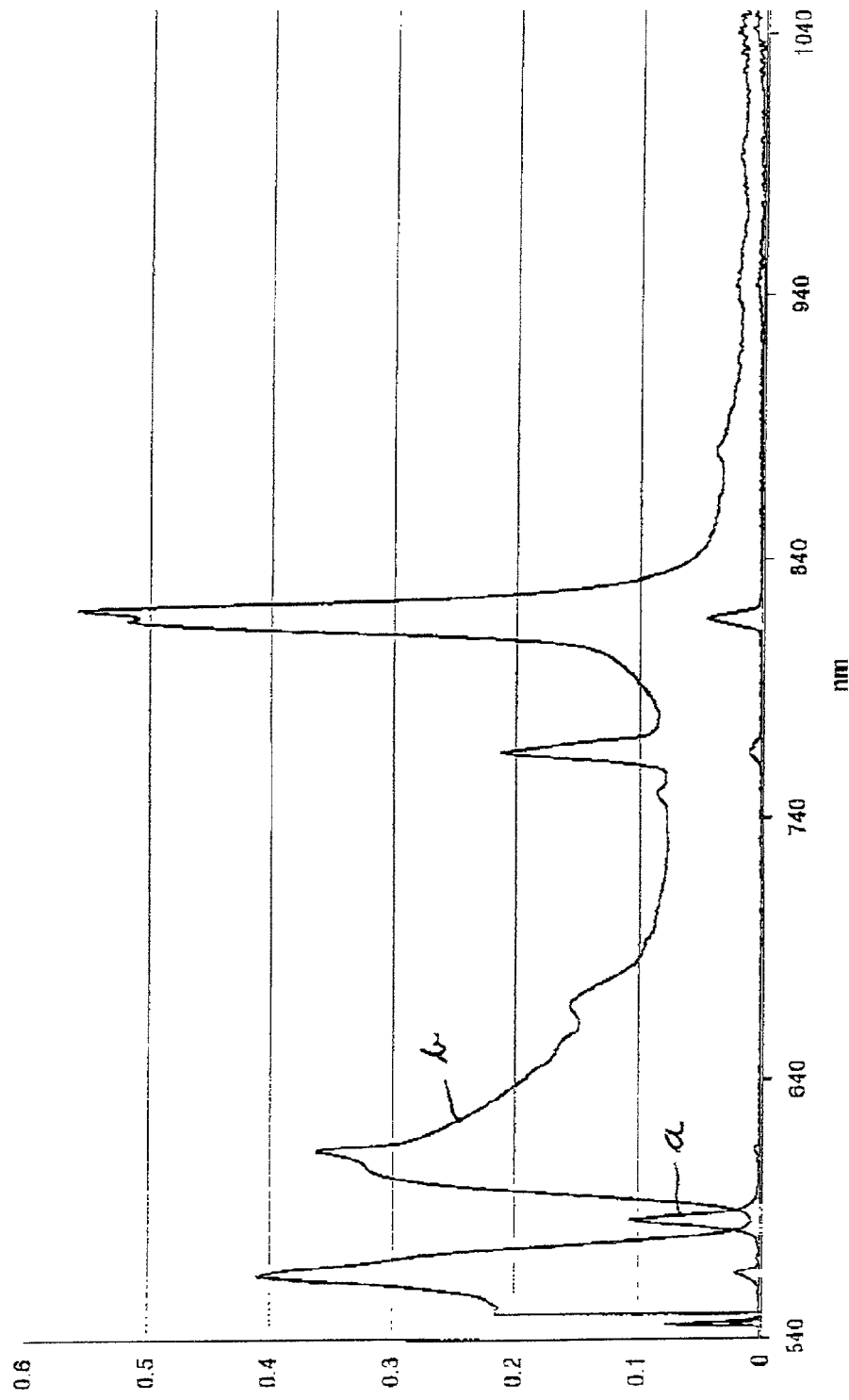
FIG. 8 is a graph relative irradiance of a sodium vapor pressure lamp in cw- and pulse overload operation.

In contrast, FIG. 8 shows the different behavior of a sodium vapor lamp. Curve b) shows that pulsed operation with 700 W using a lamp with normal operation power of 230 W induces a complete inversion of the sodium spectral emission around 488 nm. For comparison, curve a) shows the relative irradiance at cwoperation under normal power conditions.

Figure 9:
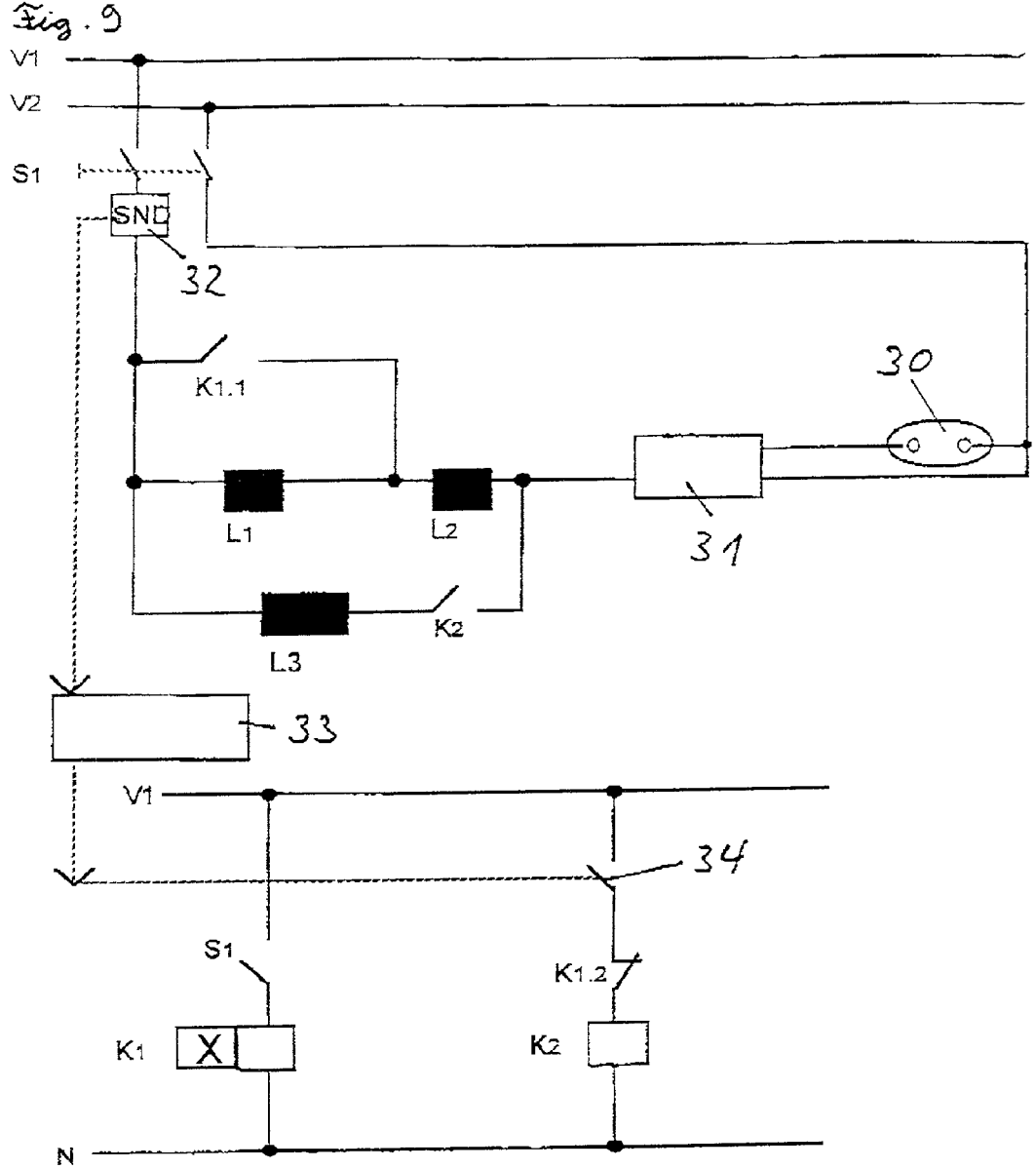
FIG. 9 is a schematic illustration of a circuit design for pulse operation of a gallium iodide doped mercury lamp with two phases of a three phase current.

FIG. 9 shows a circuit arrangement for the pulsed overload operation of a gall iumiodide-doped mercury lamp. The circuit includes a gall iumiodide-doped mercury lamp 30, an ignition device 31, a zero current detector 32, a pulse generator 33, a first relay K1 and a second relay K2, a starter switch S1 and a pulse switch 34. Both relays K1 and K2 are connected to a neutral conductor N and the first phase of a three-phase circuit. The galliumiodide-doped mercury lamp 30 is connected to the second phase V2 of the three-phase-circuit via an auxiliary contact. Via a second auxiliary contact of the starter switch S1 the first phase V1 is connected to the ignition device 31 via the zero current detector 32 via a coil arrangement. The coils L1 and L2 are connected in series. A third coil L3 is connected in parallel to the aforementioned serial coils and is switched with the contact K2 which belongs to the second relay K2. In parallel to the first coil L1 there is another contact K1.1 which relates to the first relay K1. A second contact K1.2 which belongs to the first relay K1 is switched between the second relay K2 and the pulse switch 34. The principal function of this circuit arrangement is described as follows: By closing the starter switch S1, the related auxiliary contacts also close. Therefore, the contact K1 closes and the contact K1.2 opens resp. stays open. The first phase V1 of the three phase circuit is connected via the closed contact K1.1 through coil L2 with the ignition device 31. In this arrangement coil L2 functions as an inductive coil limiting the lamp current. This switching condition remains until the galliumiodide-doped mercury lamp 30 has reached normal operational conditions. Then the relay K1 opens which may be a passing make contact. The opening of relay K1 induces the opening of the contact K1.1 and the simultaneous closing of contact K1.2. This activates relay K2 and the coil L1 is switched in series to coil L2. In this arrangement, coil L2 acts as a simmer coil. Since the pulse switch 34 is still open, the contact K2 also remains open. In this condition, the galliumiodide-doped mercury lamp 30 operates in a simmer mode. Pulsed operation is started by the pulse generator 33, if the zero current detector 32 detects zero current at the first phase V1 of the three-phase circuit. Now the pulse switch 34 switches and through activation of relay K2, the contact K2 is closed. Now the coil L3 is switched in a parallel manner, which lowers the total inductivity of the arrangement. Through this, the ignition device 31 receives an overload pulse. At the end of the pulse, the pulse generator 33 opens the pulse switch 34. This closes contact K2 and the galliumiodidedoped mercury lamp 30 operates again through the serial arrangement of coils L1 and L2 as long as the next pulse is being generated by the pulse generator 33.

FIG. 10 shows an alternative embodiment with a capacitor bank. All elements which relate to FIG. 9 have been given the same numbers. In contrast to the embodiment in FIG. 9 a TRIAC 35 is arranged between the ignition device 31 and the galliumiodide-doped mercury lamp 30. The TRIAC driver 36 is triggered by the pulse generator 32. The capacitor bank 38 is connected to the electrodes of the galliumiodide-doped mercury lamp 30 via an IGBT 37 resp. the coil L3. The driver 39 of the IGBT 37 is also triggered by the pulse generator 33. The functioning of the device is as follows: Again, the starter switch S1 is closed, which also closes K1.1 and opens the contact K1.2. The activated TRIAC 35 allows the operation of the galliumiodide-doped mercury lamp 30 under normal load. After that, the relay K1 opens, the contact K1.1 opens and K1.2 closes. 5 The galliumiodide-doped mercury lamp 30 is being operated in a simmer mode via the serial arrangement of coils L1 and L2 while the pulse generator 33 is activated. In order to allow pulse operation, the zero current detector 32 detects zero current and transmits this information to the pulse generator 33. This generator activates the drivers 33 and 39 in a way that the TRIAC 35 blocks and the IGBT 37 contacts. This switches the capacitor bank to the galliumiodide-doped mercury lamp 30 and disconnects the lamp from the supply voltage. At the end of a pulse, the IGBT 37 blocks and TRIAC 35 conducts in a way that the galliumiodide-doped mercury lamp 30 is operating in simmer mode again via coils L1 and L2. It is understood that the coils in the aforementioned technical example relate to general inductivities which could be realized differently. For demonstration of the magnitudes the following examples for the coils L1, L2 and L3 are given: L1=500 mH; L2=150 mH and L3=7 mH The following values for current resp. current density resulting from this arrangement are given below. Line 3 gives the values for normal cw-operation as a comparison.

Pulse operation: Ieff=40 A resp. 11.8 A/cm$^2$, I$_{peak}$=55 A resp. 16.2 A/cm$^2$ Simmer mode: Ieff=1.2 A resp. 0.35 A/cm$^2$, I$_{peak}$=1.7 A resp. 0.5 A/cm$^2$ normal operation: Ieff=5 A resp. 1.5 A/cm$^2$, I$_{peak}$=7 A resp. 2 A/cm$^2$

The invention claimed is:

1. Irradiation device for the treatment of acne, acne scars and skin aging, comprising at least one source of irradiation wherein the radiation source (2) emits a broadband optical spectrum in a wavelength range between at least 320 nm to at least 540 nm, the radiation source being pulse operable and/or movable in relation to the area to be irradiated, the pulse energy of which is between 0.05-10 J/cm2 and the peak irradiation intensity of the optical pulses being higher than 0.5 W/cm2 and lower than 100 kW/cm2;
wherein the device comprises a vibration device for the generation of a mechanical vibration which is placed onto the skin to be treated for facilitating the extraction of the sebum from the pores.

2. Irradiation device according to claim 1, wherein the effective pulse length is between 1 µs-500 ms.

3. Irradiation device according to claim 2, wherein the irradiation source (2) is timed with a frequency of 0.01-100 Hz.

4. Irradiation device according to claim 1, wherein the radiation source (2) is a xenon or deuterium flashlamp or a galliumiodide-doped mercury lamp which is overload operated.

5. Irradiation device according to claim 1, wherein the radiation source (2) has a device for the suppression of parts of the spectrum in the range between 320-400 nm and/or the transformation of the UV parts of the spectrum into visible light.

6. Irradiation device according to claim 5, wherein said irradiation source has a fluorescent foil in front of the irraditation source.

7. Irradiation device according to claim 6, wherein the fluorescent foil is made of silicone elastomere and doped with anorganic fluorescent particles.

8. Irradiation device according to claim 6 wherein the fluorescent foil (8) is doped with at least one of (i) the following fluorescents, fluorescing in the spectral range between 370-460 nm: Sr$_2$P$_2$O$_7$:Eu, Sr$_5$(PO$_4$)$_3$Cl:Eu, BaMg$_2$Al$_{16}$O$_{27}$:Eu, CaWO$_4$:Pb;(Sr,Ca,Ba)$_5$(PO$_4$)$_3$Cl:Eu;Sr$_2$P$_2$O$_7$:Sn,(Ba,Ca)$_5$(PO$_4$)$_3$Cl:Eu),
(ii) the following fluorescents, fluorescing in the spectral range between 510-560 nm: ZnSiO$_4$:Mn;MgAl$_{11}$O$_{19}$:Ce,Tb,Mn;YBO$_3$:Tb;LaPO$_4$:Ce,Tb,
or (iii) the following fluorescents, fluorescing in the spectral range between 610-670 nm: Y$_2$O$_3$:Eu;Y(P,V)O$_4$:Eu; CaSiO$_3$:Pb,Mn; (Sr,Mg)$_3$(PO$_4$)$_2$: Sn; 3.5MgO*0.5MgF$_2$*GeO$_2$:Mn.

9. Irradiation device according to claim 1, wherein the irradiation device (1) is provided with a device for topical and/or inhalative oxygen administration.

10. Previously presented) Irradiation device according to claim 1, wherein the irradiation device (1) is provided with a cooling device for the cooling of the irradiation area (7).

11. Irradiation device according to claim 10, wherein the cooling device is an air cooler or a water cooler.

12. Irradiation device according to claim 1, wherein the vibrations are generated time-shifted to pulse emission.

13. Irradiation device according to claim 1, wherein said vibration device is an electrodynamic or photoelastic transducer.

14. Method for the treatment of acne, acne scars or the cosmetical treatment of the skin, particularly for the treatment of skin wrinkles, epidermal and dermal atrophy, skin coarseness, pigmentation disorders, telangiectasias, flabbiness of skin and enlarged pores by means of a pulsable broadband optical radiation source (2) which emits pulses at pulse energies between 0.05-10 J/cm2 in a wavelength range between 320-at least 540 nm, the peak radiation power of the optical pulses being between 0.5 W/cm2 and 100 kW/cm2, comprising the following procedural steps:
a) irradiation of the acne with effective pulse lengths between 1 µs-500 ms at pulse frequencies between 0.01-100 Hz for at least 60 minutes,
b) placing a vibration device onto the skin to be treated for the generation of a mechanical vibration;
c) vibrating the skin to be treated with the vibration device and removing sebum from the pores of said skin; and
d) at least one repetition of step a) after 24 hours.

15. Method according to claim 14, wherein the wavelength of the emitted radiation is higher than 400 nm.

16. Method according to claim 14, wherein before and/or during the irradiation the oxygen concentration in the acne area is enhanced by topical and/or inhalatory administration of oxygen.

17. Irradiation according to claim 6, wherein the irradiation device (1) is provided with a cooling device for the cooling of the irradiation area (7) and/or the luminescent foil.

18. Irradiation device according to claim 1,
wherein the effective pulse length is between 1 µs-500 ms,
wherein the irradiation source (2) is timed with a frequency of 0.01-100 Hz,
wherein the radiation source (2) is a xenon or deuterium flashlamp or a galliumiodide-doped mercury lamp which is overload operated,
wherein the radiation source (2) has a device for the suppression of parts of the spectrum in the range between 320-400 nm and/or the transformation of the UV parts of the spectrum into visible light,
wherein the said radiation source has a fluorescent foil in front of the radiation source,
wherein the fluorescent foil is made of silicone elastomer and doped with organic fluorescent particles,
wherein the fluorescent foil (8) is doped with at least one of (i) the following fluorescents, fluorescing in the spectral range between 370-460 nm: Sr$_2$P$_2$O$_7$:Eu, Sr$_5$(PO$_4$)$_3$Cl:Eu, BaMg$_2$Al$_{16}$O$_{27}$:Eu, CaWO$_4$:Pb;(Sr,Ca,Ba)$_5$(PO$_4$)$_3$Cl:Eu;Sr$_2$P$_2$O$_7$:Sn,(Ba,Ca)$_5$(PO$_4$)$_3$Cl:Eu),
(ii) the following fluorescents, fluorescing in the spectral range between 510-560 nm: ZnSiO$_4$:Mn;MgAl$_{11}$O$_{19}$:Ce,Tb,Mn;YBO$_3$:Tb;LaPO$_4$:Ce,Tb,
or (iii) the following fluorescents, fluorescing in the spectral range between 610-670 nm: Y$_2$O$_3$:Eu;Y(P,V)O$_4$:Eu; CaSiO$_3$:Pb,Mn; (Sr,Mg)$_3$(PO$_4$)$_2$:Sn; 3.5MgO*0.5MgF$_2$*GeO$_2$:Mn,
wherein the irradiation device (1) is assigned a device for topical and/or inhalative oxygen administration,
wherein the irradiation device (1) is assigned a device for cooling of the of the irradiation area (7) and/or the luminescent foil,
wherein the cooling device is an air cooler or a water cooler, wherein the irradiation device has assigned a device for the generation of a mechanical vibration which is placed onto the skin to be treated, wherein the vibrations are generated time-shifted to pulse emission, and wherein said vibration device is an electrodynamic or photoelastic transducer.

19. Method according to claim 14, wherein the wavelength of the emitted radiation is higher than 400 nm, and wherein before and/or during the irradiation the oxygen concentration in the acne area is enhanced by topical and/or inhalatory administration of oxygen.

20. Irradiation device according to claim 6, wherein the fluorescent foil (8) is doped with at least one of (i) a fluorescent fluorescing in the spectral range between 370-460 nm, (ii) a fluorescent fluorescing in the spectral range between 510-560 nm or (iii) a fluorescent fluorescing in the spectral range between 610-670 nm.

* * * * *